United States Patent [19]

Marxer et al.

[11] Patent Number: 4,941,488

[45] Date of Patent: Jul. 17, 1990

[54] TENSILE THREAD HOLDER FOR TOOTH CARE

[76] Inventors: Rochus Marxer, Römerstrasse 217, FL-9485 Nendeln; Reinhard Franck, Heiligkreuz 51, FL-9490 Vaduz, both of Liechtenstein

[21] Appl. No.: 178,496

[22] Filed: Apr. 7, 1988

[30] Foreign Application Priority Data

Apr. 17, 1987 [AT] Austria ................................ 982/87

[51] Int. Cl.⁵ ............................................. A61C 15/00
[52] U.S. Cl. .................................................. 132/323
[58] Field of Search ............... 132/323, 324, 325, 326, 132/327

[56] References Cited

U.S. PATENT DOCUMENTS

| | | | |
|---|---|---|---|
| 1,815,408 | 7/1931 | Jordan | 132/323 |
| 4,013,085 | 3/1977 | Wright | 132/323 |
| 4,427,018 | 1/1984 | Lagace | 132/323 |
| 4,655,233 | 4/1987 | Laughlin | 132/323 |

FOREIGN PATENT DOCUMENTS

| | | | |
|---|---|---|---|
| 1095460 | 12/1960 | Fed. Rep. of Germany | 132/323 |
| 44159 | 6/1927 | Norway | 132/323 |

*Primary Examiner*—John J. Wilson
*Attorney, Agent, or Firm*—Toren, McGeady & Associates

[57] ABSTRACT

Tensile threads used for tooth care can be fastened to a fork-type holder. The ends of each thread have thickened portions in the form of knots which rest as abutments when the thread is placed in the holder on the fork-type arms. For storing the threads in a hygenically closable container, a plurality of threads are arranged spaced apart from each other and parallel to each other. The knots on each side of the threads are located in a row and are connected to each other through intended breaking points. The threads are placed in closable containers from which they can be moved individually by means of the fork-type holder. After the threads have been removed by the holder, the holder assumes it correct position of use.

1 Claim, 2 Drawing Sheets

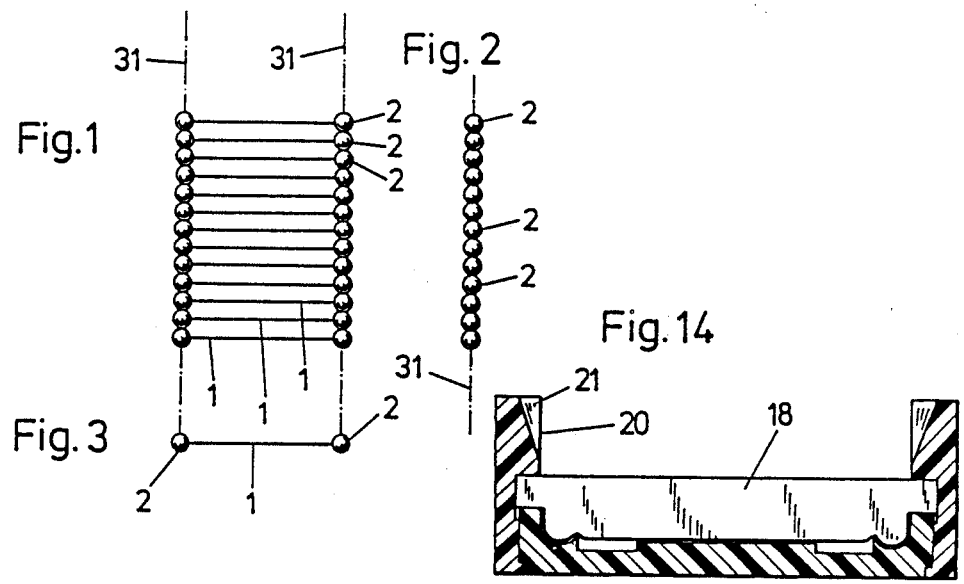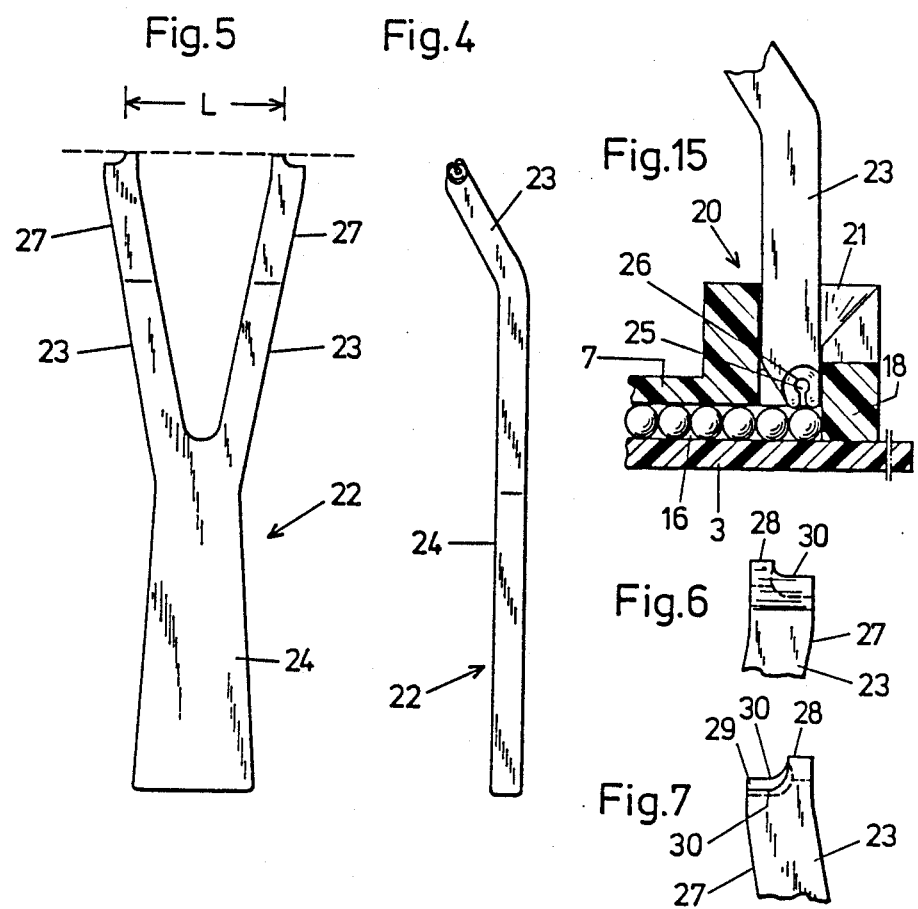

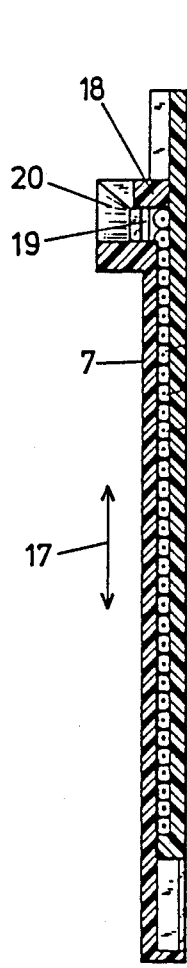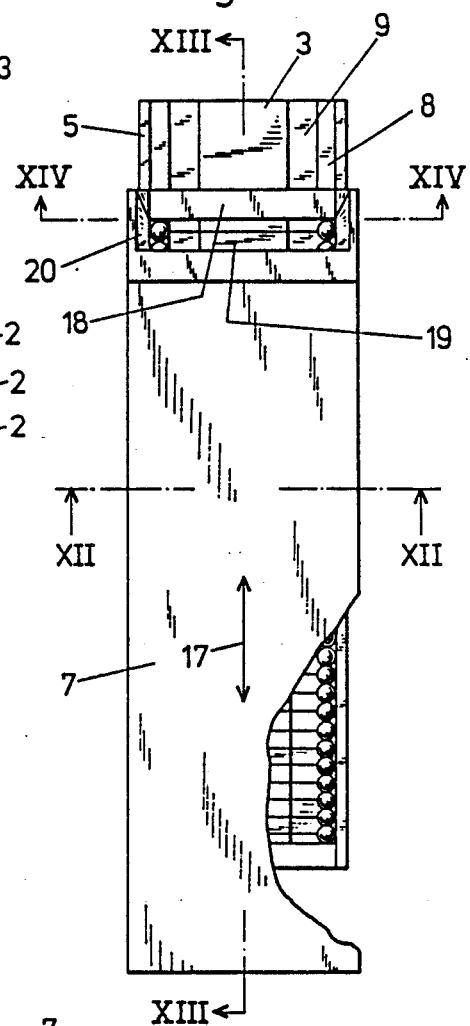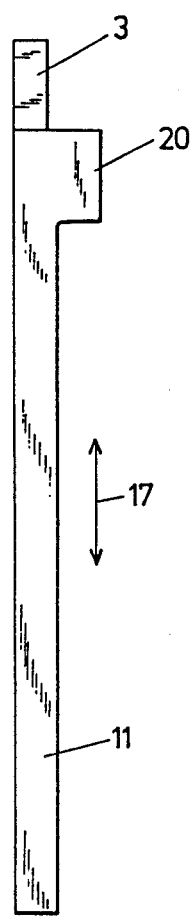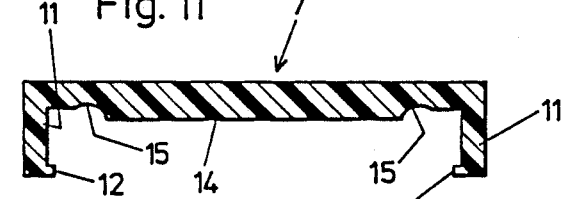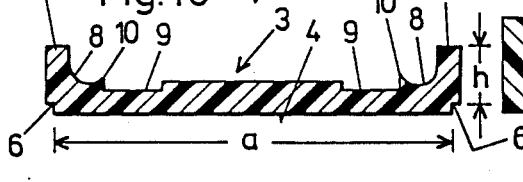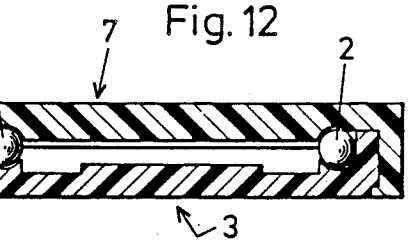

TENSILE THREAD HOLDER FOR TOOTH CARE

BACKGROUND OF THE INVENTION

1. Field of the Invention

The present invention relates to a tensile thread for tooth care, particularly for cleaning the spaces between teeth. The thread is to be mounted in a stirrup-type or fork-type holder. The ends of the thread have thickened portions, preferably in the form of spherical knots which rest as abutments when the thread is placed in the holder on the stirrup-type or fork-type arms thereof. The present invention further relates to a container for receiving tensile threads and to a holder for using the tensile thread.

2. Description of the Prior Art

Devices for tooth care, particularly for cleaning between teeth, are known. These devices include a stirrup-type or fork-type holder with freely cantilevering arms whose ends hold a tightened silk or plastic thread. The free ends of the arms each have a slot into which the ends of the thread can be placed. The thread is supported by winding a portion thereof several times around the arm, as described in U.S. Pat. Nos. 2,650,598 and 2,180,522 and in German Offenlegungsschrift No. 28 42 404.

Instead of being wound around the arm, the thread received by the holder may have knot-type thickened portions at the ends which prevent the thread from sliding out of the slots which receive the thread. These knots have the function of abutments. For regulating or adjusting the tension of the threads, the arms of the holder supporting the thread can be moved relative to each other by means of screws or spreading members, as disclosed in U.S. Pat. No. 3,631,869.

As described in U.S. Pat. Nos. 4,508,125 and 4,512,354 and British Pat. No. 525,528, it is also known to provide the holder with a hollow grip and to place a roll of this thread into the hollow space with the piece of thread required for tooth cleaning being pulled from this roll.

Finally, U.S. Pat. No. 3,769,396 and German Offenlegungsschrift No. 22 14 244 describe known arrangements and devices for manufacturing the above-described knot-like thickened portions at the ends of the threads.

Starting from the above-described prior art, it is an object of the present invention to provide a tensile thread which can be stored and removed from the storage as needed for the use of the thread. In addition, the thread is to be hygienically stored and the holder proper is to be constructed in such a way that it supplements the thread and can be inserted in the holder for removing the threads stored in the holder without requiring complicated manipulations.

SUMMARY OF THE INVENTION

In accordance with the present invention, a plurality of tensile threads are arranged spaced apart from each other and parallel relative to each other for storage purposes, the threads having a length which corresponds approximately to the mounting length in the holder. The knots provided at each end of the threads are located on the two sides thereof on a line each and the knots located immediately adjacent to each other on one side of this row of threads are connected to each other in reduced-diameter intended breaking points. Accordingly, the individual threads form a ladder-like structure, wherein the individual threads initially are all connected to each other at the spherical knots. When the threads are to be used, they can be separated from each other at the intended breaking points.

The container according to the present invention for receiving the tensile threads for tooth care includes a box-like base member with a bottom and longitudinal side walls which extend parallel to each other. Groove-like indentations which extend adjacent on the inside and parallel to the longitudinal side walls are provided in the base member. A cover member extends over and in a positively locking manner along the longitudinal side walls of the base member. The base member and the cover member can be moved relative to each other and parallel to the plane of the base member. The cover member has at one end thereof a portion which closes the inner cross-sectional area of the base member at least in the region of the groove-like indentations. A slot-like opening is provided in the cover member adjacent this portion, the length of the opening corresponding at least to the length of the tensile thread. The inner side of the cover member forms together with the groove-like indentations in the base member a duct for receiving the spherical knots of the threads.

As a result, the ladder-like structure of threads can be hygienically stored in the container.

A holder according to the present invention for removing a thread each from the container includes two fork-like arms whose free ends define slots for receiving the thread. The slots are provided in spherically-shaped, outwardly facing indentations. Relative to the outer edges of the arms, the indentations are offset toward the middle of the stirrup-type or fork-type arms. The arms further include shoulder surfaces adjacent the spherical indentations. The shoulder surfaces are offset relative to the outer ends of the arms and are concavely arched. Parallel edges between the shoulder surfaces define sharp cutting edges.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there is illustrated and described a preferred embodiment of the invention.

BRIEF DESCRIPTION OF THE DRAWING

In the drawing:

FIG. 1 is an elevational view of a ladder-like arrangement of threads as the threads are arranged for storage purposes;

FIG. 2 is a side view of the threads of the threads of FIG. 1;

FIG. 3 is a top view of the threads of FIG. 1;

FIG. 4 is a side view of a holder according to the present invention;

FIG. 5 is an elevational view of the holder of FIG. 4;

FIG. 6 is a front view, on a larger scale, of the free ends of the arms of the holder of FIGS. 4 and 5;

FIG. 7 is a rear view, on a larger scale, of the free ends of the arms of the holder of FIGS. 4 and 5;

FIG. 8 is an elevational view of a container according to the present invention, with a portion of the cover member broken away;

FIG. 9 is a side view of the container of FIG. 8;

FIG. 10 is a sectional view on a larger scale taken through the cover member of the container;

FIG. 11 is a sectional view on a larger scale taken through the base member of the container;

FIG. 12 is sectional view on a larger scale taken through the container along sectional line XII—XII of FIG. 8;

FIG. 13 is a longitudinal sectional view taken through the container along sectional line XIII—XIII of FIG. 8;

FIG. 14 is a sectional view on a larger scale taken through the container along sectional line XIV—XIV of FIG. 8; and FIG. 15 is a partial sectional view showing the removal of a thread from the container by means of the holder.

DETAILED DESCRIPTION OF THE INVENTION

FIG. 1 of the drawing shows a plurality of threads 1 of silk or a synthetic material. The threads 1 are arranged parallel to each other and spaced apart from each other and have spherical knots 2 at the ends. The knots 2 are of plastics material and are connected to each other along line 31. The connections between the knots are at reduced-diameter intended breaking points. Accordingly, the threads 1 having knots 2 at the ends thereof define a connected ladder-type structure. Such a structure can be manufactured with conventional means. The length of the individual threads 1 corresponds to the mounting length L illustrated in FIG. 5.

A box-type container is used for storing this sensitive ladder-type structure hygienically and protected against mechanical influences. The container and its individual components are illustrated in FIGS. 8 through 14. The container has a base member 3 illustrated in detail in FIG. 10, with a bottom 4 and side walls 5. Base member 3 has at its lower longitudinal edges a step-like inwardly directed recess 6 which is engaged in a positively locking manner by a cover member 7, as shall be described in more detail below.

Groove-like indentations 8 extend along the inside and parallel to the longitudinal side walls 5. Bottom 4 of base member 3 has toward the middle of base member 3 additional grooves 9 extending parallel and next to the groove-like indentations 8. The depth of each indentation 8 measured relative to the inwardly located edge 10 of the indentation 8 is smaller than half the diameter of each knot 2. The spacing a between the centers of the indentations 8 corresponds approximately to the length of a thread 1 including its knots 2.

Cover member 7 is U-shaped, as shown in FIG. 11. The free lower ends of the side walls 11 of cover member 7 have ledge-like projections 12 which are directed toward each other and which engage the recesses 6 of the base member 3 when the container is properly assembled. The ledge-like projections 12 may have inclined surfaces or edges facing each other, so that, when the container is being assembled, the side walls 11 are forced slightly outwardly when the cover member 7 is forced from the top against the base member 3 and, when the projections 12 have traveled along the height h of the base member 3, the projections 12 can engage in recesses 6 in order to create the desired positively locking connection. In practice, the wall thicknesses of cover member 7 and base member 3 will be substantially thinner than illustrated in the drawing; the relatively large wall thicknesses shown in the drawing have been selected to increase the clarity of the drawing.

As FIG. 11 of the drawing further shows, the inner side 14 of cover member 7 also has groove-like indentations 15 located at locations corresponding to the groove-like indentations 8 in the base member 3. The indentations 8 and 15 in the base member 3 and the cover member 7, respectively, together form a circular duct 17 for receiving the knots 2.

As can be seen from FIG. 13, the inner length of the container is a multiple of the diameter of the knots 2 arranged at the ends of the threads 1. Accordingly, a large number of threads can be arranged within the container in a row or a plane. Cover member 7 and base member 3 are slidable relative to each other, as indicated by arrow 17 in FIGS. 8, 9 and 13.

FIGS. 13 and 14 show that the cover member 7 additionally has near one end thereof a portion 18 which closes off the inner cross-sectional area of the base member 3 at least in the region of the groove-like indentation 8. A slot-like opening 19 is provided in the cover member 17 adjacent portion 18. Opening 19 extends along the width of the cover member 7 and its length is at least the same as the length of the thread 1 insulating the knots 2. The width of the slot-like opening 19 in cover member 7 corresponds at least to the diameter of a knot 2 at the ends of thread 1. Toward the top, the slot-like opening 19 continues into an insertion chute 20, wherein at least the inner walls forming the narrow sides 21 of the insertion chute 20 converge toward the slot-like opening 19.

While, in the embodiment illustrated in FIG. 12, the cover member 7 engages with its side walls 11 over the base member 3, it is also possible to have a cover member which seen in cross-section has a circumferentially closed contour, wherein the cover member entirely surrounds the base member, so that the cover member and the base member together form a sliding box of the matchbox type.

A ladder-type structure composed of threads 1 and knots 2, as shown in FIGS. 1 to 3, is placed in the initially open base member 3, wherein the knots 2 are received by the groove-like indentations 8. The length of the ladder-type structure is selected so that the base member is covered along its entire length with the structure. Subsequently, as explained above, the cover member 7 is pressed onto the base member 3. The container is now filled and ready for use.

FIGS. 4 and 5 of the drawing show a holder 22 which includes a handle 24 and two fork-like arms 23 which receive the thread, as schematically illustrated with a broken line in FIG. 5. Starting from the free end faces of the arms 23 are slots 25 which are located in externally arranged spherical indentations 26.

The illustrations of FIGS. 6 and 7 show that the spherical indentations 26 are offset relative to the outer edges 27 of the arms 23 toward the middle of the stirrup-type or fork-type arms. Concavely arched shoulder surfaces 29 which are offset relative to the outer ends 28 of the arms are provided laterally outwardly adjacent the spherical indentations 26. Essentially parallel edges 30 which border the shoulder surfaces 29 are constructed as cutting edges.

FIG. 15 is a partial sectional view showing how a thread 1 is removed by means of the holder 22 through the insertion chute 20. Base member 3 has been slid relative to cover member 7 to such an extent that the transversely extending portion 18 of the cover member 7 rests against the knots 2 of the first thread. The fork-like arms 23 are now inserted in the insertion chute 20, wherein the inclined narrow sides 21 of the insertion chute force the arms 23 slightly together in the plane of the fork, so that the spacing between the free ends of the arms with the slots 25 is slightly reduced. As the holder is inserted, the shoulder surfaces 29 are placed above the knots 2 of the first thread which rests against portion 18. The holder is now pushed further until the sharp edge 30 rests against the intended breaking point between the knots 2. When the shoulder 22 is now suddenly forced in further, the sharp edge 30 cuts the above-mentioned intended breaking point and the holder can now penetrate with its free ends until the free ends are received in the groove 9 of the base member 3. As a result, the knots 2 of the first thread resting against portion 18 are received in the spherical indentations and the thread connecting the knots is received in the slots 25. When the holder 22 is now pulled back out of the insertion chute 20, the holder takes the thread with it and, as soon as the holder leaves the insertion chute 20, the free ends of the arms 23 can move outwardly and, thus, tighten the thread which is now ready for its intended use.

While the above description refers to a cover member and a base member, and the specific structural elements of these members, it is within the scope of the invention to exchange the base member and the cover member and to provide the relatively deep groove-like indentations 8 in the cover member 7. The depth of the indentations 8 is selected in such a way that the thread 1 can extend freely tensioned between its two knots 2 within the container, as illustrated in FIG. 12.

After the thread resting against portion 18 has been removed, the base member 3 is moved farther relative to cover member 7 until the next thread, or rather the knots 2 of the next thread, rest against portion 18. Thus, portion 18 forms a kind of abutment which prevents the knots of the respectively first thread from moving when the holder is inserted into the insertion chute 20 and is forced into this chute. Because of the groove 9 next to the groove-like indentations 8, the holder can be inserted sufficiently deeply into the container in spite of the shape of the arms of the holder shown in FIGS. 6 and 7, so that the spherical knots of the respectively first thread are always securely and reliably grasped.

Although the knots 2 are disclosed above as being spherical, the knots are not limited to this shape. The knots are understood to be portions of increased thickness compared to the thread materials.

While a specific embodiments of the invention has been shown and described in detail to illustrate the application of the inventive principles, it will be understood that the invention may be embodied otherwise without departing from such principles.

We claim:

1. A holder for receiving a tensile thread for tooth care, particularly for cleaning the spaces between teeth, the ends of the thread having thickened portions in the form of spherical knots, a plurality of tensile threads arranged in a row spaced apart from each other and parallel relative to each other, the threads having a length which corresponds approximately to the mounting length in the holder, the knots located immediately adjacent to each other on each side of the row of threads being connected to each other in reduced-diameter intended breaking points, the holder comprising two fork-like arms with free ends, the free ends defining slots for receiving the thread, wherein the slots are provided in spherically-shaped outwardly facing indentations for receiving the spherical knots of the threads, the arms defining outer edges, the indentations being offset toward the middle of the fork-type arms relative to the outer edges of the arms, the arms having shoulder surfaces adjacent the spherical indentations, the shoulder surfaces being offset relative to the outer ends of the arms and being concavely arched, and parallel edges formed between the shoulder surfaces defining sharp cutting edges for cutting the intended breaking points.

* * * * *